United States Patent [19]

Yoshida

[11] Patent Number: 4,615,986

[45] Date of Patent: Oct. 7, 1986

[54] METHOD FOR COMPETITIVE PROTEIN BINDING ASSAYS INHIBITING NON-SPECIFIC INTERFERENCE

[75] Inventor: Robert A. Yoshida, Mountain View, Calif.

[73] Assignee: Syntex (U.S.A.) Inc., Palo Alto, Calif.

[21] Appl. No.: 692,941

[22] Filed: Jan. 18, 1985

Related U.S. Application Data

[60] Division of Ser. No. 411,180, Aug. 25, 1982, Pat. No. 4,508,892, which is a continuation of Ser. No. 17,874, Mar. 5, 1979.

[51] Int. Cl.$^4$ .................. G01N 33/53; G01N 33/544; G01N 33/542

[52] U.S. Cl. .................................. 436/500; 436/529; 436/537; 436/800; 436/823

[58] Field of Search ............... 436/537, 529, 500, 800, 436/823

[56] References Cited

U.S. PATENT DOCUMENTS 4,152,411  5/1979  Schall, Jr. ........................... 436/537
4,160,016  7/1979  Ullman ................................ 436/537

OTHER PUBLICATIONS

Smith, FEBS Letters, vol. 77(1), pp. 25-27, (May, 1977).

Primary Examiner—Christine M. Nucker
Attorney, Agent, or Firm—Bertram I. Rowland; Theodore J. Leitereg

[57] ABSTRACT

Conjugates of heavy atoms containing analytes or their analogs and fluorescent molecules are covalently bonded to macromolecular supports to minimize the interference of fluorescence during assays, due to non-specific binding of serum proteins to the conjugate.

7 Claims, No Drawings

METHOD FOR COMPETITIVE PROTEIN BINDING ASSAYS INHIBITING NON-SPECIFIC INTERFERENCE

This is a division of copending application U.S. Ser. No. 411,180 filed Aug. 25, 1982 now U.S. Pat. No. 4,508,892, which is a continuation of prior application U.S. Ser. No. 017,874 filed on Mar. 5, 1979.

BACKGROUND OF THE INVENTION

1. Field of the Invention

It is known that when a heavy atom is able to contact a fluorescer, quenching results. This phenomenon can be employed in any assay, where a ligand or ligand analog of interest naturally has a heavy atom, such as iodine, or the heavy atom is synthetically introduced. By preparing a conjugate of the heavy atom containing ligand and a fluorescer, a relatively low level of fluorescence is observed, when the conjugate is irradiated with light at a wavelength which results in excitation of the fluorescer. However, when antiligand is bound to the ligand in the conjugate, a substantial enhancement of fluorescence is observed.

With polyiodothyronines, the iodine present is capable of quenching fluorescence, hen the polyiodothyronine is covalently bonded to a fluorescer. However, when attempting to use this reagent in a serum sample for determining polyiodothyronines, non-specific binding of serum proteins to the conjugate results in variation in the observed fluorescence unrelated to the amount of ligand present. Due to patient sample variation, the degree to which the observed fluorescence changes at constant ligand concentration varies with the source of the serum. Therefore, it is necessary to find some means to inhibit the non-specific effect of the serum proteins on the observed results.

2. Description of the Prior Art

U.S. Pat. No. 3,988,943 describes a competitive protein binding assay employing ligand-fluorescer conjugates, where the binding of antiligand inhibits the binding of antifluorescer. U.S. Pat. No. 3,996,345 describes an immunoassay employing a chromophore pair, where the chromophores are related by one of the chromophores quenching the fluorescence of the other one of the chromophores, where the amount of quencher brought within quenching distance of the fluorescing chromophore is related to the amount of analyte in the sample. Robbins, "Thyroxine-binding Proteins", Trace Components of Plasma: Isolation and Clinical Significance, Alan, R. Liss, Inc., New York, page 331 (1976) postulated that the inability of prealbumin to bind thyroxine-agarose affinity gels was related to the inability of the thyroxine to orient properly in the protein binding site. Co-pending application Ser. No. 824,576, filed Aug. 13, 1977, teaches the use of a polyiodothyronine-fluorescer conjugate for the determination of polyiodothyronines based on the enhancement of fluorescence when anti(polyiodothyronine) binds to the polyiodothyronine.

SUMMARY OF THE INVENTION

An improved method is provided for fluorescent immunoassays involving a conjugate of a ligand analog with a fluorescer, where the ligand analog has a heavy atom which results in the quenching of the fluorescer. When antiligand binds to ligand, fluorescence is enhanced. In the presence of serum proteins, sample to sample fluorescent variation is observed which interferes with the determination of analyte. The non-specific interference is substantially diminished by bonding of the ligand analog-fluorescer conjugate to a polysaccharide support. Sensitive assays are provided for polyiodothyronines, as well as for serum capacity for binding thyroxine.

Compositions and kits are provided for use in the subject assays.

DESCRIPTION OF THE SPECIFIC EMBODIMENTS

Methods and compositions are provided for determining heavy atom containing ligands and receptors for such ligands, where a fluorescent label is employed, which is conjugated to the heavy atom containing ligand. Interference from serum proteins is inhibited by bonding the ligand analog-fluorescer conjugate to a polysaccharide support and using the resulting support-bound-conjugate as a fluorescent reagent for the determination of ligand and/or receptor.

Depending upon whether ligand or receptor is of interest, the assay procedure may vary.

Where receptor is of interest, which receptor is other than antibody (IgG), so that serum capacity for binding of the ligand is of interest, the method will involve combining the serum sample, a pre-determined amount of ligand, antiligand, the ligand-fluorescer conjugate bonded to support, and optionally antifluorescer. A rate or equilibrium mode may be employed so that either the rate of change in the amount of fluorescence can be determined or the absolute amount of fluorescence can be determined once the system shows only a small variation in fluorescence with time.

This mode is particularly applicable with and may be exemplified by an assay referred to as triiodothyronine (T-3) uptake, which is part of a thyroid function profile. In effect, by adding a predetermined amount of triiodothyronine to a serum sample, where the triiodothyronine is in excess of the available serum binding capacity for thyroxine, the binding sites of the serum proteins will be substantially saturated. There will be residual triiodothyronine which is then determined by providing for a competition between the residual triiodothyronine and the triiodothyronine-fluorescer conjugate bonded to the polysaccharide support for antibodies for triiodothyronine. The binding of the antibodies to the triiodothyronine conjugate results in an enhancement of fluorescence, which enhancement is related to the amount of residual triiodothyronine. Optionally, one may add antifluorescer to quench any of the conjugate which is not bound to antiligand. In addition, a quenching chromophore may be conjugated to the antifluorescer to further insure substantially complete quenching of any fluorescer bound to antifluorescer.

Where ligand or ligand receptor is to be measured directly, one need only combine the sample suspected of containing the analyte-ligand and ligand receptor or ligand receptor—with the ligand—fluorescer conjugate bonded to the support, and the ligand receptor when ligand is the analyte, and determine the enhancement of fluorescence or optionally, add antifluorescer as described above.

By determining the fluorescence, either as a rate or equilibrium mode, as compared to one or more samples having known amounts of capacity or analyte, one can provide a standard curve, so that the observed fluorescence may be translated into a value for the binding capacity of a sample.

DEFINITIONS

Analyte—any compound or group of compounds having similar structure which is to be measured.

Receptor—any compound or group of compounds which are capable of specifically binding to a particular spatial and polar organization. Receptors include antibodies, enzymes, specific binding proteins, such as the like. Where antibodies are involved, these receptors will be referred to as antiligand.

Ligand—an organic compound for which a receptor naturally exists or can be prepared, which may be haptenic or antigenic.

Fluorescer—a compound which is capable of receiving energy, either as quanta of light or from another molecule in an excited state, referred to as a donor molecule, which may be a chemiluminescer, to be excited and return to the ground state by emission of a photon.

Quencher—a molecule which is able to accept energy from a donor molecule, which donor molecule is capable of fluorescence, and by the acceptance of the energy inhibits the fluorescence of the fluorescer molecule.

Heavy Atom—an atom which is capable of stable covalent bonding to an organic molecule and which by contact with a fluorescer molecule inhibits the fluorescence of the molecule by, for example, intersystem crossing.

Ligand Analog—a modified ligand, which may be modified by more than substitution of a hydrogen atom with the compound to which it is conjugated and which has a sufficient proportion of the spatial and polar organization of the ligand, so as to be able to compete with the ligand for ligand receptor. Particularly, the ligand is modified to introduce a functionality which permits the ligand to be conveniently bonded to the fluorescer and/or support.

Support-ligand analog-fluorescer ("support-conjugate")—a heavy atom containing ligand or ligand analog is covalently bonded to a fluorescer and the resulting conjugate covalently bonded to a polysaccharide macromolecular soluble or swellable support. The support will normally be in excess of about $3 \times 10^4$, usually in excess of $1 \times 10^5$ molecular weight.

METHOD

Methods are provided for determining the presence of a ligand, receptor for the ligand, or serum protein binding capacity for the ligand. The ligand or its analog must either naturally have a heavy atom or be capable of being modified by introduction of a heavy atom to form a ligand analog-conjugate with a fluorescer. The subject method finds particular use with polyiodothyronines having from 2 to 4 iodine atoms, particularly 3 to 4 iodine atoms i.e. triiodothyronine (T-3) and thyroxine (T-4).

In the mode for determining serum binding capacity, an aqueous buffered assay medium is provided which includes the serum sample, ligand at least equal to the binding capacity of the serum, antiligand, and the support-ligand analog-fluorescer conjugate, and optionally antifluorescer. While various orders of addition of the reagents may be employed, preferably the ligand and serum are combined in an aqueous medium, followed by antiligand, followed by the support-conjugate, and optionally followed by the antifluorescer. Desirably, the first two stages will have incubations to allow for substantial equilibration of the system. Where antifluorescer is added, there will be a third incubation after addition of the support-conjugate.

Where a direct measure of ligand or receptor is involved, the sample suspected of containing the analyte, and the reciprocal member of the specific binding pair are combined with the support-conjugate, optionally followed by the addition of antifluorescer. One or more incubation steps may be involved.

Various dilutions and incubations may be employed in the assay. That is, before or concomitantly with each addition, additional aqueous medium may be added to provide for accurate transfer of reagents, increase of the volume as required by the measuring instrument, or the like. Incubation steps will normally vary from about 0.5 min to 6 hrs, more usually from 1 min to 1 hr, preferably from about 5 min to 0.5 hr, more preferably from about 10 min to 0.5 hr.

The aqueous assay medium may have up to 40% of an organic polar solvent, usually an oxy solvent i.e. hydroxylic or ethereal, such as ethanol, diethyl ether, tetrahydrofuran, glycerol, etc.

The aqueus medium will normally be buffered in the range of about 5 to 10, more usually in the range of about 6 to 9.5, and preferably in the range of about 7 to 9.5. Various buffers may be used, although one buffer may be preferred over another buffer in a particular situation. Illustrative buffers include borate, phosphate, barbital, tris, etc.

The temperatures during the various stages of additions and measurements will generally be in the range of about 10° to 50° C., more usually in the range of about 15° to 45° C., and preferably in the range of about 15° to 40° C.

As indicated previously, the order of addition will vary widely, depending upon the particular materials employed, the manner of measurement, rate or equilibrium, and the like. However, the support-conjugate will normally not be added to antiligand in the absence of the analyte, nor will antifluorescer be added prior to combining the support-conjugate with antiligand.

MATERIALS

Macromolecular support

Various polysaccharide supports may be employed, which are natural products, modified natural products, or synthetic materials, which are water soluble or insoluble, usually at least water swellable.

Illustrative supports include dextran, agarose, sepharose, starch, amylopectin, and the like. Naturally occurring materials may be modified by cross-linking, degradation, functionalization, and the like.

Molecular weights will normally be at least 35,000, more usually at least 50,000, and normally not exceed about 2,000,000, more normally not exceeding about 1,000,000.

Fluorescer-Quencher

Fluorescers of interest fall into a variety of categories having certain primary functionalities. These primary functionalities include 1- and 2-aminonaphthalene, p,p'-diaminostilbenes, pyrenes, quaternary phenathridine salts, 9-aminoacridines, p,p-diaminobenzophenone imines, anthracenes, oxacarbocyanine, merocyanine, 3-aminoequilenin, perylene, bis-benzoxazole, bis-p-oxazolyl benzene, 1,2-benzophenazin, retinol, bis-3-aminopyridinium salts, hellebrigenin, tetracycline, sterophenol, benzimidazolylphenyl, 2-oxo-3-chromen, indole, xanthene, 7-hydroxycoumarin, phenoxazine, salicylate, strophanthidin, porphyrins, triarylmethanes and flavin.

Individual fluorescent compounds which have functionalities for linking or can be modified to incorporate such functionalities include dansyl chloride, fluoresceins such as 3,6-dihydroxy-9-phenylxanthhydrol, rhodamineisothiocyanate, N-phenyl 1-amino-8-sulfonatonaphthalene, N-phenyl 2-amino-6-sulfonatonaphthalene, 4-acetamido-4-isothiocyanatostilbene-2,2'-disulfonic acid, pyrene-3-sulfonic acid, 2-toluidinonaphthalene-6-sulfonate, N-phenyl, N-methyl 2-aminonaphthalene-6-sulfonate, ethidium bromide, atebrine, auromine, 2-(9'-anthroyl)palmitate, dansyl phosphatidylethanolamine, N,N'-dioctadecyl oxacarbocyanine, N,N'-dihexyl oxacarbocyanine, merocyanine, 4-(3'-pyrenyl)-butyrate, d-3-amino-desoxyequilenin, 12-(9'-anthroyl)-stearate, 2-methylanthracene 9-vinylanthracene, 2,2'-(vinylene-p-phenylene)bis-benzoxazole, p-bis-2-(4-methyl-5-phenyl oxazolyl)benzene, 6-dimethylamino-1,2-benzophenazin-retinol, bis(3'-aminopyridinium)-1,10-decandiyl diiodide, sulfonaphthyl hydrazone of hellebrigenin, chlortetracycline, N-(7-dimethylamino-4-methyl-2-oxo-3-chromenyl)maleimide, N-p-(2-benzimidazolyl)-phenyl meleimide, N-(4-fluoroanthyl)-maleimide, bis(homovannilic acid), reazurin, 4-chloro-7-nitro-2.1.3-benzoxadiazole, mercyanine 540, resorufin, rose bengal, and 2,4-diphenyl-3(2H)-furanone.

The fluorescing chromogen will preferably absorb light at wavelengths longer than 350 nm, preferably longer than 400 nm, and particularly preferred longer than 450 nm. The extinction coefficient is preferably greater than $10^4$ above 400 nm, preferably greater than $10^4$ above 450 nm and more preferably greater than $10^5$ above 400 nm. Preferably, the fluorescer emits light above 400 nm, more preferably above 450 nm.

It should be noted that the absorption and emission characteristics of the dye may vary from being free in solution and being bound to a colloidal particle. Therefore, when referring to the various wavelength ranges and characteristics of the dyes, it is intended to indicate the dyes as employed and not the dye which is unconjugated and characterized in an arbitrary solvent.

The quencher molecule will normally also be a fluorescent molecule, but will have an absorption band which overlaps the emission band of the fluorescer. Therefore, rhodamine is a quencher for fluorescein. The quenching occurs due to dipole-dipole interactions through space and over a distance of less than 100 Å. Therefore, having chosen a fluorescer, and having determined its emission band, one choses a quencher which has an absorption band with substantial overlap of the emission band of the fluorescer.

Fluorescer-T-3 conjugate

Depending upon the nature of the fluorescer, a wide variety of linking groups may be employed for preparing the fluorescer-T-3 conjugate. T-3 has four available sites for linking: the carboxy, amino, hydroxy and the 5' position of the aromatic ring. For the most part, the positions employed for conjugation will be one or both of the amino group and the carboxyl group.

The fluorescer molecules are commercially available with a wide variety of functionalities or can be modified to introduce such functionalities. Therefore, depending upon the functionality present in the fluorescer group, different linking groups may be employed. For the most part, the linking groups will be relatively short, varying from a bond to one to 12 atoms in the chain, more usually 1 to 6 atoms in the chain where the group consists of carbon, hydrogen, oxygen, nitrogen and sulfur, being aliphatic, alicyclic, aromatic or heterocyclic, usually aliphatic, either saturated or unsaturated, usually having from 0 to 1 site of ethylenic unsaturation, and having from 0 to 6, more usually 0 to 4 heteroatoms which are oxygen, nitrogen, and sulfur, wherein oxygen will be present bonded solely to carbon, as oxy or non-oxo-carbonyl, nitrogen will be present bonded only to carbon and hydrogen, as amido or amino, preferably tertiary amino, and sulfur will be analogous to oxygen. Preferably, the linking group will be an aliphatic hydrocarbon group having the appropriate functionalities at the terminal sites of the linking group for bonding the T-3 and the fluorescer.

For the most part, the functionalities employed for bonding will be alcohols, amines, carboxylic acid groups, oximino ethers, oxo-carbonyls, particularly by reductive amination, sulfuryl groups, active halogen, mercaptans, and active olefins. Methods for employing these various functionalities for linking are well known in the literature and do not require exemplification here.

The following is a list of illustrative groups which could be used for linking T-3 with the fluorescer, in accordance with the nature of the functionality present in the fluorescer molecule.

TABLE 1

| Functionalities on T-3 and Fluorescer | Linking Group |
|---|---|
| $NH_2;NH_2$ | —CO— |
| | $CO(CH_2)_nCO$—; n = 0–4 |
| | $—CH_2(CH_2)_nCO$—; n = 0–4 |
| | $—CONH(CH_2)_nCO$—; n = 1–4 |
| | $—CSNH(CH_2)_nCO$—; n = 1–4 |
| | $—C(NH)(CH_2)_nCO$—; n = 0–4 |
| | $—CO(CH_2)_nN(CH_3)(CH_2)_nCO$—; = 1–2 |
| | $—CO(CH_2)_nO(CH_2)_nCO$; n = 1–2 |
| | $—C(NH)(CH_2)_nCH_2$—; n = 1–4 |
| $NH_2;CO_2H$ | $—CO(CH_2)_nNH$—; n = 1–4 |
| | $—CH_2(CH_2)_nO$—; n = 1–4 |
| | $—CH_2(CH_2)_nNH$—; n = 1–4 |
| | $—C(NH)(CH_2)_nNH$—; n = 1–4 |
| | $—CSNH(CH_2)_nNH$—; n = 1–4 |
| | $—CO(CH_2)_nNHCO(CH_2)_nNH$; n = 1–2 |
| $CO_2H;C::C$ | $—NH(CH_2)_nS$—; n = 2–4 |
| | $—O(CH_2)_nS$—; n = 2–4 |
| $CO_2H;CO_2H$ | $—NH(CH_2)_nNH$—; n = 2–5 |
| | $—O(CH_2)_nO$—; n = 2–5 |
| | $—O(CH_2)_nNH$—; n = 2–5 |

It is understood, that the above table is not exhaustive, but merely illustrative of the more likely linking groups. Furthermore, while methylene groups are indicated, it is to be understood that the methylene groups may be substibuted with alkyl groups, particularly methyl groups, there normally not being more than about 1 to 2 alkyl substituents. Furthermore, while the chain links indicated are the preferred links, there may be situations where the chains could be further extended.

For the most part, the fluorescer-T-3 conjugate will have the following formula:

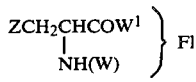

wherein:
Z is 3,3',5-triiodo-p-phenoxyphenol, bonded at the 1 position to the methylene;
one of W and $W^1$ is a linking group, and when not a linking group W is hydrogen and $W^1$ is hydroxyl or lower alkoxy of from 1 to 3 carbon atoms; and
Fl is a fluorescent molecule, particularly a fluorescein.

The linking groups have been described previously.

Support-T-3-fluorescer conjugate

The T-3 fluorescer conjugate may be conjugated to either a functionality present on the T-3 or on the fluorescer. Since the T-3 has two convenient functionalities, an amino group and a carboxyl group, for the most part, the functionality of the T-3 which has not been employed for conjugating to the fluorescer may be employed for conjugating to the support. The hydroxylic groups of a wide variety of supports can be further functionalized to introduce additional functionalities, such as amino groups, carboxylic acid groups, mercapto groups, and the like. Therefore, except for the fact that one also has the possibility for linking to hydroxyl groups, the same types of linking groups may be employed, depending upon the functionalities present on the support. Preferably, amino substituted supports will be employed, because of the possibility of obtaining stable inert links to the support.

The compositions of this invention will for the most part have the following formula:

wherein:
Z has been defined previously;
the Support has been described previously and may be any one of a variety of polysaccharide supports which are modified natural products, or synthetic materials, which are water soluble or insoluble and at least water swellable, preferably dextran, sepharose, agarose, starch, amylopectin and the like, naturally occurring or modified by cross-linking, functionalization, degradation or the like and more preferably functionalized with a linking group having 1 to 6 carbon atoms and usually providing an amino or non-oxo carbonyl;
one of $W^2$ and $W^3$ is a linking group to the support, and when not a linking group, one of $W^2$ and $W^3$ is of the formula:

Fl—X— wherein Fl is a fluorescer as described previously and X is a linking group as described previously; and
m is one to the molecular weight of the support divided by about 5,000, preferably divided by about 10,000, and usually not exceeding 20 with supports under 200,000 molecular weight; usually not exceeding 10 with supports under 100,000 molecular weight.

A preferred group of compositions has the following formula:

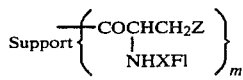

wherein
Z, X, Fl, Support and m have been defined previously, and the carbonyl has an ester or amide bond, preferably an amide bond to the Support.

Of particular interest in the subject invention are compounds of the following formula:

wherein:
Z has been defined previously;
$Support^x$ includes the definition of support and is further limited in that it is of from about 30,000 to 200,000 molecular weight, more usually of about 35,000 to 100,000 molecular weight, and is particularly dextran;
$X^1$ is a bond or linking group of from 2 to 6, more usually of from 2 to 4 carbon atoms, preferably an aliphatic aminoacid and $Fl^1$ is of the formula:

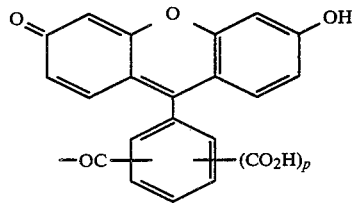

wherein:
p is 0 or 1 and the non-oxo-carbonyl groups are preferably 2,5, (the 1 position of the phenyl bonded to the xanthine) with the non-oxo-carbonyl group bonded to the linking group, being bonded preferably to an amine to form an amide linkage.

Receptor

The receptors are generally relatively large molecules which are capable of specifically recognizing a spatial and polar organization and capable of binding preferentially to such organization. In the subject invention, the receptors will normally be antibodies or naturally occurring proteins which bind to a specific hapten. The whole antibody may be employed or a Fab fragment. The receptor may be unmodified or modified by conjugation to a quencher. Quenchers have been described previously.

Kits

In order to provide enhanced sensitivity and accuracy, the materials employed in the assay may be provided as kits. That is, the materials are prepared in predetermined ratios to enhance the response with variation in concentration over the range of interest.

The subject kits will have the support-T-3-fluorescer conjugate, antifluorescer, and anti-T-3. The antibodies will normally be lyophilized and may be present by themselves or in combination with an appropriate amount of buffer, stabilizers, or the like. The amount of buffer will be related to the dilution of the antibody to provide the aqueous reagent at the appropriate concentration. Normally, the antibodies will be in separate containers.

The ratio of anti(T-3) to the T-3 as part of the support conjugate will generally be in the range of about 0.2 to 5 mole:mole, more usually in the range of about 0.5 to 1 mole:mole. The amount of anti-fluorescer in relation to the amount of fluorescer present as support-conjugate will generally be present in from about 0.5 to 5 mole:mole, more usually 0.75 to 3 mole:mole.

The following examples are offered by way of illustration and not by way of limitation.

EXPERIMENTAL

All temperatures not otherwise indicated are in centigrade. All percents and parts not otherwise indicated are by weight, except when two liquids are combined, and the percents are by volume. The following abbreviation is employed:

T-3-3,3′,5-triiodo-L-thyronine.

Ex. 1. Amination of BHP-Activated Dextran 70

BHP-Activated Dextran 70 (0.250 g, from Pharmacia, 70,000 molecular weight) was dissolved in 5.0 ml of 0.15M ammonia in 0.10M $NaHCO_3$—$Na_2CO_3$, adjusted to pH 9.0. The solution was stirred at room temperature for 18 hours. 35 $\mu l$ of $\beta$-mercaptoethanol was added to the reaction mixture to give a 0.10M solution of the thiol. The reaction mixture was then stirred at room temperature for 10 hours, after which the reaction mixture was exhaustively dialyzed against deionized $H_2O$ at room temperature. The resulting amino-Dextran 70 was found to contain 0.91 moles amino groups per mole of Dextran 70, by the TNBS amino content determination (Snyder, S. L. and Sobocinski, P. Z., *Anal. Biochem.*, 64: 284 (1975), using 1-amino-2-propanol as standard and by the Orcinol sugar content determination (Glazer, A. M., et al., *Chemical Modification of Proteins, Selected Methods and Analytical Procedures*, North-Holland, Amsterdam (1975)) using BHP-Activated Dextran 70 as standard.

Ex. 2. The Preparation of $T_3$-Fluorescein

A. Preparation of NHS Esters of 6-Carboxyfluorescein

Dicyclohexylcarbodiimide (0.548 g, $2.66 \times 10^{-3}$ mole, Aldrich) was added to 1.0 g ($2.66 \times 10^{-3}$ mole) of 6-carboxyfluorescein (Eastman) and 0.306 g ($2.66 \times 10^{-3}$ mole) of N-hydroxysuccinimide (NHS) (Aldrich) in 6.0 ml of dry THF/DMF (1:1). After stirring for three hours at room temperature, the reaction mixture was cleared of insoluble urea by filtration and the solvent removed in vacuo. The resulting oil was taken up in 10–15 ml of ethyl acetate and was put on a $4.0 \times 45$ cm silica gel (60–200 mesh) column. Elution with ethyl acetate at gravity flow initially yielded NHS ester, while later fractions yielded a mixture of the NHS ester and unreacted acid. The initial fractions were pooled and solvent removed in vacuo. The resulting oil was azeotropically dried with benzene yielding pure NHS ester (mixture of isomers) in a 63% yield. The isomeric NHS esters were separated by chromatography on a $4.0 \times 46$ cm silica gel column, eluting with acetic acid/acetone/benzene (2:25:73), with a flow rate of 1.8 ml/minute. Eight ml fractions were collected yielding a separation between the isomers. The isomer-containing fractions were stored overnight at $-20°$ and yielded the two separated isomers as crystalline solids. The solids were separately isolated by filtration to give 0.260 g (21% yield) of isomer I and 0.209 g (17% yield) of isomer II. Isomer I is orange and Isomer II is yellow. NHS esters had Rf values of 0.33 and 0.27, respectively, on $5 \times 20$ cm silica gel plates (Sil G-25, no binder) when irrigated with acetic acid/acetone/benzene (2:25:73).

B. Conjugation of Fluorescein-NHS Ester (Isomer II) to T-3

6-Carboxyfluorescein NHS ester (0.060 g, $1.3 \times 10^{-4}$ mole) isomer II was added to 0.091 g ($1.4 \times 10^{-4}$ mole) of $T_3$ (Sigma) in 2.0 ml of dry DMF containing 39 $\mu l$ ($2.8 \times 10^{-4}$ mole) of triethylamine. After stirring for two hours at room temperature, 25–30 ml of 1.0M HCl was added to the reaction mixture to yield a heavy flocculent precipitate. After filtering off the product by suction, the solid was washed once with 10 ml of 1.0M HCl, then thrice with 10 ml portions of deionized water. The product was dried in vacuo at room temperature and then purified by chromatography on a $4.0 \times 46$ cm silica gel column eluted with acetic acid/isopropanol/dichloromethane (2:10:88), at a flow rate of 3 ml/minute. The product-containing fractions were pooled and the solvent removed in vacuo. The resulting oil was azeotropically dried with benzene to yield a solid. The resulting solid was taken up in 10 ml of DMF and then precipitated by the addition of 30 ml of 1.0M HCl. The product was filtered off and washed with 10 ml 1.0M HCl and three 10 ml portions of deionized water. After drying in vacuo as described above, 0.079 g (68%) of product was obtained. $T_3$-fluorescein (isomer II) had a Rf value of 0.43 on silica gel plates ($5 \times 20$ cm) irrigated with acetic acid/isopropanol/dichloromethane (2:10:88).

Ex. 3. NHS Ester of $T_3$-Fluorescein

N-Hydroxysuccinimide in dry THF (27 $\mu l$, 0.19M, $5.1 \times 10^{-6}$ mole) and 27 $\mu l$ ($5.2 \times 10^{-6}$ mole) of 0.19M dicyclohexylcarbodiimide in THF were added to $5.1 \times 10^{-3}$ g ($5.0 \times 10^{-6}$ mole) of $T_3$-fluorescein in 0.50 ml of dry THF. The reaction mixture was stirred in a stoppered flask at 2°–4°, for 18 hours. Examination by thin layer chromatography (tlc, acetic acid:acetone:benzene, 2:30:68) on silica gel plates (Sil G-25, no binder) indicated the formation of two products of Rf 0.32 and 0.45. Benzylamine treatment of a small quantity (10 $\mu l$) of the reaction mixture caused the disappearance of these two products and the appearance of a single major product of Rf 0.37. The data suggests the presence of the NHS ester and azalactone.

Ex. 4. The Preparation of $T_3$-Fluorescein-Dextran 70

The NHS ester solution prepared in Example 3 (50 $\mu l$, $4.60 \times 10^{-7}$ mole) was added to 1.0 ml ($2.1 \times 10^{-7}$ mole amino groups) of $2.3 \times 10^{-4}$M amino-Dextran 70 (70,000 m.w.) and 1.0 ml of 0.10M $NaHCO_3$—$Na_2CO_3$(pH 9.0) at room temperature. The reaction mixture was stirred at room temperature for 45 minutes and then put onto $2.6 \times 25$ cm Sephadex G-25 (Pharmacia) gel in deionized $H_2O$ and eluted with deionized water. The unretarded orange band was collected and concentrated in 2.4 ml, and then treated with 0.80 ml ($1.6 \times 10^{-3}$ mole) of 2.0M hydroxylamine (pH 7.0) for 45 minutes at room temperature. The hydroxylamine-treated conjugate was then twice gel filtered on a $2.0 \times 21$ cm Sephadex G-25M column as described above. The resulting $T_3$-fluorescein-Dextran 70 conjugate was found to contain 0.25 mole of $T_3$-fluorescein per mole of Dextran 70 as determined by UV determination for the fluorescein chromophore and by the Orcinol sugar content determination, using BHP-activated Dextran 70 as standard.

In order to demonstrate the efficacy of compounds prepared in accordance with the subject invention, the conjugate was employed in a series of T-3 uptake assays. In carrying out the assay all UV data was obtained using a Cary 15 UV-Visible spectrophotometer, while endpoint fluorescence data was obtained using a Perkin-Elmer Model 1000 Fluorimeter equipped with bandpass filters giving $\lambda_{ex}=491$ nm and $\lambda_{em}=519$ nm. Rate fluorescence data was obtained using a modified Varian Fluorichrom fluorimeter, equipped with bandpass filters giving $\lambda_{ex}=491$ nm and $\lambda_{em}=530$ nm. The rate fluorimeter was interfaced to a Hewlett-Packard 9815A calculator, equipped with a linear least squares program for analysis of fluorimeter data, over a specified interval of time. A delay time of 5 seconds and a read time of 55 seconds was used for all rate fluorescence work and the work was done at ambient temperature.

The following solutions are prepared as reagents for use in the assay.

Buffer: 35 mM sodium barbital-HCl containing 0.10% egg albumin and 0.01% $NaN_3$(pH 7.5); Prepared using deionized water and was Millipore filtered (0.22 μl cellulose acetate filters), prior to use Solutions & Dilutions: All prepared using 0.01M $NaH_2PO_4$—$Na_2HPO_4$ containing 0.15M NaCl, 0.01% $NaN_3$, and 0.10% egg albumin (pH 7.1)

The protocol employed for carrying out an assay is as follows:

A sample, 20 μl, is drawn up into a diluter and dispensed with 200 μl of buffer into a Croan cup. Into the Croan cup is introduced 20 μl of the T-3 dilution with 200 μl of buffer. After a 15-minute incubation period 20 μl of anti-T-3 dilution is introduced with 200 μl of buffer. The assay reagents are allowed to incubate at room temperature for 30 minutes and 20 μl of $2.2 \times 10^{-}M$ $T_3$-fluorescein-Dextran 70 and 200 μl buffer were then added followed by a 30 minute incubation period at room temperature. Anti-fluorescein (20 μl) antibody and 200 μl buffer were added to the assay mixture, followed by immediate aspiration into the fluorimeter.

This procedure was followed with 10 fresh Red Cross samples of human serum. The results gave the following statistics:

number of samples, n=10
average fluorescence rate, $\Delta F=627.2$
standard deviation, $\sigma=6.44$
% coefficient of variation, %C.V.=1.03

The data demonstrate that the serum-to-serum variations of the fluorescence rate are within experimental error.

Table 1 shows the comparative results of T-3 dose responses run in the absence and presence of 1.8% human serum (Red Cross Pool).

TABLE 1

($T_3$-F-Dextran) = 4.0 nM
0.1 μl ANTI-$T_3$ IgG
FLUORESCENCE RATE

| ($T_3$) nM | 0% Human Serum | 1.8% Human Serum |
|---|---|---|
| 0 | 570 | 575 |
| 1 | 490 | 510 |
| 2 | 385 | 420 |
| 3 | 245 | 330 |
| 4 | 125 | 230 |
| 5 | 65 | 150 |
| 6 | 50 | 125 |
| 7 | 50 | 110 |

It is evident from the above results, that the compositions of the subject invention provide for reagents which can be used in a sensitive immunoassay for determining serum binding capacity in which the rate of fluorescence is related to the amount of ligand present and non-specific interference is substantially diminished.

Although the foregoing invention has been described in some detail by way of illustration and example for purposes of clarity of understanding, it will be obvious that certain changes and modifications may be practiced within the scope of the appended claims.

What is claimed is:

1. In an assay of a serum sample involving a conjugate of a fluorescent molecule and a ligand analog having a heavy atom capable of quenching the fluorescence of said fluorescent molecule, wherein said quenching is subject to variation due to serum sample variation, wherein the assay is performed by:

A. combining in an aqueous medium to form an assay solution:
  1. said sample,
  2. said conjugate, and
  3. ligand receptor;
B. exciting said fluorescer, and
C. measuring the amount of light emitted from said assay solution at at least one wavelength as compared to the amount of light emitted from an assay solution having a known amount of ligand, the improvement comprising a support comprising a ligand analog-fluorescer conjugate covalently bonded to a macromolecular polysaccharide support having a molecular weight of at least 35,000 and not exceeding 2,000,000, said ligand analog-fluorescer conjugate comprising a fluorescent molecule that absorbs light having a wavelength longer than 350 nanometers with an extinction coefficient above $10^4$ and emits light having a wavelength longer than 400 nanometers, said fluorescent molecule being covalently bonded to a ligand that is a modified hapten or antigen having a heavy atom capable of quenching said fluorescent molecule by inhibiting the fluorescence of said fluorescent molecule upon contact therewith.

2. A method for determining in an assay the thyroxine binding capacity of a serum sample comprising:

A. combining in an aqueous medium to form an assay solution:
  1. said sample,
  2. an amount of T-3 at least equal to about said thyroxine binding capacity,
  3. anti-T-3, and
  4. a support comprising comprising a T-3 analog-fluorescer conjugate covalently bonded to a macromolecular polysaccharide support having a molecular weight of at least 35,000 and not exceeding 2,000,000, said T-3 analog-fluorescer conjugate comprising a fluorescent molecule that absorbs light having a wavelength longer than 350 nanometers with an extinction coefficient above $10^4$ and emits light having a wavelength longer than 400 nanometers, said fluorescent molecule being covalently bonded to T-3 that is capable of quenching said fluorescent molecule by inhibiting the fluorescence of said fluorescent molecule upon contact therewith;

B. exciting said fluorescer; and

C. measuring the amount of light emitted from said assay solution at at least one wave length as compared to the amount of light emitted from an assay solution having a known thyroxine binding capacity.

3. A method for determining the presence of a ligand or ligand receptor in a serum sample suspected of containing said ligand or ligand receptor wherein said ligand or its analog has a heavy atom capable of quenching a fluorescer molecule, comprising:

A. combining in an aqueous medium to form an assay solution:
   1. said serum sample,
   2. a support comprising a ligand analog-fluorescer conjugate covalently bonded to a macromolecular polysaccharide support having a molecular weight of at least 35,000 and not exceeding 2,000,000, said ligand analog-fluorescer conjugate comprising a fluorescent molecule that absorbs light having a wavelength longer than 350 nanometers with an extinction coefficient above $10^4$ and emits light having a wavelength longer than 400 nanometers, said fluorescent molecule being covalently bonded to a ligand that is a modified hapten or antigen having a heavy atom capable of quenching said fluorescent molecule by inhibiting the fluorescence of said fluorescent molecule upon contact therewith, and
   3. ligand-receptor B. exciting said fluorescer; and C. measuring the amount of light emitted from said assay solution at at least one wavelength as compared to the amount of light emitted from an assay solution having a known amount of ligand.

4. Method according to claim 1 wherein an anti-fluorescer is combined with said aqueous assay solution.

5. Method according to claim 2 where an anti-fluorescer is combined with said aqueous assay solution.

6. Method according to claim 3 wherein an anti-fluorescer is combined with said aqueous assay solution.

7. A method for determining in an assay the thyroxine binding capacity of a serum sample comprising:

A. combining in an aqueous medium to form an assay solution:
   1. said sample,
   2. an amount of T-3 at least equal to about said thyroxine binding capacity,
   3. anti-T-3, and
   4. a compound of the formula:

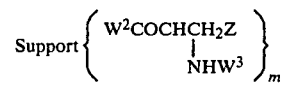

wherein:

Z is 3,3',5'-triiodo-p-phenoxyphenol, bonded at the 1 position to the methylene;

Support is a polysaccharide having a molecular weight of at least 35,0000 and not exceeding 2,000,000;

one of $W^2$ and $W^3$ is a bond or linking group to Support, wherein such linking group has from 1 to 12 atoms in a chain which atoms are selected from the group consisting of carbon, hydrogen, oxygen, nitrogen, and sulfur, and when one of $W^2$ and $W^3$ is not a linking group, one of $W^2$ and $W^3$ is of the formula:

$$Fl-X-$$

wherein Fl is a fluorescent molecule that absorbs light having a wavelength longer than 350 nanometers with an extinction coefficient greater than $10^4$ and emits light having a wavelength longer than 400 nanometers and X is a bond or linking group having from 1 to 12 atoms in a chain, which atoms are selected from the group consisting of carbon, hydrogen, oxygen, nitrogen, and sulfur; and m is an integer between one and the molecular weight of the Support divided by about 500.

* * * * *